(12) United States Patent
Prusty et al.

(10) Patent No.: US 11,185,476 B2
(45) Date of Patent: Nov. 30, 2021

(54) DENTAL COMPOSITE

(71) Applicants: NEWSOUTH INNOVATIONS PTY LIMITED, Sydney (AU); THE UNIVERSITY OF SYDNEY, New South Wales (AU)

(72) Inventors: Bellasanty Gangadhara Prusty, Little Bay (AU); Ginu Rajan, Wollongong (AU); Paul Shouha, Bardwell Park (AU); Ayman Ellakwa, Seven Hills (AU)

(73) Assignees: Newsouth Innovations Pty Limited, Sydney (AU); The University of Sydney, Sydney (AU)

( * ) Notice: Subject to any disclaimer, the term of this patent is extended or adjusted under 35 U.S.C. 154(b) by 0 days.

(21) Appl. No.: 16/757,071

(22) PCT Filed: Oct. 19, 2018

(86) PCT No.: PCT/AU2018/051141
§ 371 (c)(1),
(2) Date: Apr. 17, 2020

(87) PCT Pub. No.: WO2019/075528
PCT Pub. Date: Apr. 25, 2019

(65) Prior Publication Data
US 2020/0261324 A1 Aug. 20, 2020

(30) Foreign Application Priority Data
Oct. 20, 2017 (AU) .................... 2017904240

(51) Int. Cl.
*A61K 6/887* (2020.01)
*A61K 6/77* (2020.01)
*A61K 6/17* (2020.01)

(52) U.S. Cl.
CPC ............ *A61K 6/887* (2020.01); *A61K 6/17* (2020.01); *A61K 6/77* (2020.01)

(58) Field of Classification Search
None
See application file for complete search history.

(56) References Cited

U.S. PATENT DOCUMENTS

| | | | | |
|---|---|---|---|---|
| 4,064,566 A | * | 12/1977 | Fletcher | A61F 2/30767 128/898 |
| 2013/0023600 A1 | * | 1/2013 | Kobashigawa | A61K 6/891 523/116 |
| 2014/0303284 A1 | * | 10/2014 | Chavan | C08L 83/04 523/435 |

FOREIGN PATENT DOCUMENTS

| | | | | |
|---|---|---|---|---|
| EP | 0345581 | | 12/1989 | |
| EP | 2959882 | | 12/2015 | |
| EP | 2959882 A1 | * | 12/2015 | ............ A61K 6/836 |

OTHER PUBLICATIONS

International Application No. PCT/AU2018/051141, International Search Report and Written Opinion dated Nov. 22, 2018, 9 pages.

(Continued)

*Primary Examiner* — Peter A Salamon
(74) *Attorney, Agent, or Firm* — Myers Bigel, P.A.

(57) ABSTRACT

The present application describes fib-reinforced dental composites (FRCs), processes for producing and uses of, the fibre-reinforced dental composites. More particularly, the fibre-reinforced dental 5 composites described herein comprise a polymerisable resin and from about 0.5% to about 25% w/w of fibres having a diameter of from about 3 μm to about 9 μm and a length of from about 60 μm to about 2 mm.

22 Claims, 5 Drawing Sheets

(56) References Cited

OTHER PUBLICATIONS

Shouha et al., Effect of Short Glass Fibers on the Polymerization Shrinkage Stress of Dental Composite, Journal of Biomedical Materials Research Part B, vol. 105, No. 7, Oct. 2017, pp. 1930-1937.
"Extended European Search Report corresponding to European Application No. 18869335.2 dated Jul. 8, 2021".
Lassila, Lippo , et al., "Mechanical properties of fiber reinforced restorative composite with two distinguished fiber length distribution", Journal of the Mechanical Behavior of Biomedical Materials 60:331-338 (Feb. 2, 2016).

* cited by examiner

DENTAL COMPOSITE

CROSS REFERENCE TO RELATED APPLICATION

This application is a U.S. National Phase under 35 U.S.C. § 371 of International Patent Application No. PCT/AU2018/051141, filed Oct. 19, 2018, which claims priority to Australian Patent Application No. 2017904240, filed Oct. 20, 2017, the contents of all of which are incorporated herein by this reference.

FIELD OF THE INVENTION

The present invention relates to dental composites and, more particularly, to fibre-reinforced dental composites (FRCs). The present invention also relates to processes for producing, and uses of, the dental composites.

BACKGROUND

Dental composites typically comprise a polymerisable resin matrix and one or more fillers. Dental composites are used in the treatment or restoration of teeth, e.g. to form a filling in a tooth. Typically, the dental composite is positioned and shaped, and is then polymerised (cured) to harden the dental composite.

Whether driven by public aesthetic demands, concerns over amalgam's toxicity or trends toward conservative management of dentitions, dental composites have become the material most often employed in the restoration of teeth.

Tooth-coloured dental composites are now widely considered as the material of choice for the restoration of teeth. However, the strength and toughness of these materials are considered by many practitioners to be less than ideal, especially for posterior teeth restorations. In addition, due to the inherent properties of the resins used (e.g. polymerization shrinkage and resultant interfacial debonding), their use can lead to post-operative sensitivity and recurrent decay.

Dental composites are typically composed of inorganic opaque particulate fillers dispersed in a resin matrix. The fillers provide the cured dental composite with wear resistant properties as well as aesthetic properties. Dental composites typically also comprise other components, such as colourants and initiators or catalysts to initiate or catalyse the polymerisation of the resin.

Dental composite materials are typically placed and manipulated directly in the mouth and are set (i.e. cured or hardened) with curing lights having a wavelength of approximately 400-470 nm. Their use in stress bearing areas of posterior teeth is becoming an acceptable option but brittleness and a tendency to edge fracture remain important limitations for such uses.

Although relatively uncommon clinically, the use of fibres in dental composites has been studied in some fixed and removable dental prostheses. The most commonly used and studied FRCs in dentistry are indirectly manufactured (i.e. portions of cured/hardened dental composite are formed out of the mouth and then either bonded or cemented onto tooth substrate). Indirect restorations usually require more aggressive tooth preparation than direct procedures since they need to allow for precise insertion pathways. Due to operator and/or patient based limitations (such as handling difficulties and/or salivary contamination), chairside or intra-oral reinforcement of dental resins with fibres is less common still. Such chairside procedures typically involve combining dental resin with sections of fibre cut from straight or woven ultra-high molecular weight polyethylene mats.

Higher stiffness, fracture toughness and flexural strengths have been claimed for some dental composites reinforced with randomly oriented short fibres. For example: 16 GPa, 3.2 MN/m$^{3/2}$ and 176 MPa respectively for a 71% volume filled, 20-800 µm long E glass rod material [Zakaria M R, Najim W A; *J. Bagh. College Dent.* 2009; 21:18-22]. This composite comprises milled E glass fibres which have a diameter of approximately 17 µm. The uncured composite is a very viscous material making it difficult to place in a cavity of a tooth. This composite has also been found to exhibit poor wear properties due to "plucking" of the surface exposed fibres and fillers.

Another directly packable dental composite material is "EverX Posterior" by GC, Japan, which comprises E-glass fibres approximately 1-2 mm long and approximately 17 µm in diameter. Although some of its properties are acceptable, such as fracture toughness, it also has some undesirable properties, such as it being a very sticky material and very difficult to place. In plane fibre alignment in EverX Posterior material also results in anisotropic mechanical properties. For example, testing has shown that EverX Posterior exhibits significant vertical shrinkage (resulting in high vertical stress).

One of the issues negatively affecting the greater acceptance of dental composites by dental practitioners is the ease of use. For example, the dental materials currently available and recommended for use in stress bearing areas of the mouth are widely considered by practitioners to be difficult to place, highly technique sensitive and relatively difficult to finish.

It would be advantageous to provide alternative dental composites. It would be advantageous if at least preferred embodiments of the present invention were to provide a dental composite material having good strength (including flexural strength and/or elastic modulus) and durability when cured or hardened. It would also be advantageous if at least preferred embodiments of the present invention were to provide a dental composite material that is relatively easy for a practitioner to place and finish.

SUMMARY OF THE INVENTION

In a first aspect, the present invention provides a dental composite comprising:
  a polymerisable resin; and
  from about 0.5% to about 25% w/w of fibres having a diameter of from about 3 µm to about 9 µm and a length of from about 60 µm to about 2 mm.

In an embodiment, the diameter of the fibres is from about 3 µm to about 6 µm. In an embodiment, the mean fibre diameter is about 5 µm.

In an embodiment, the length of the fibres is from about 60 µm to about 750 µm.

In an embodiment, the aspect ratio (AR) of the fibres is from about 20 to about 200. In an embodiment, the aspect ratio (AR) of the fibres is from about 30 to about 100.

In an embodiment, the fibres comprise two or more populations of fibres, wherein the mean aspect ratio (AR) of one population of fibres is different to the mean aspect ratio (AR) of at least one other population of fibres. In an embodiment, the mean aspect ratio (AR) of one population of fibres is from about 20 to about 100, and the mean aspect ratio (AR) of the at least one other population of fibres is from about 70 to about 200.

In an embodiment, more than 80% w/w of the fibres have a length of from about 200 μm to about 500 μm.

In an embodiment, the fibres constitute from about 1% to about 10% w/w of the dental composite. In an embodiment, the fibres constitute about 5% w/w of the dental composite.

In an embodiment, the fibres are composed of glass. In an embodiment, the glass is selected from aluminosilicate glass, barium glass, fluorine glass, quartz, fused silica, borosilicate glass, aluminofluorosilicate glass, high calcium glass, high magnesium glass and mixtures thereof. In an embodiment, the glass is S-glass.

In an embodiment, the fibres are substantially randomly oriented in the dental composite.

In an embodiment, the fibres are fibres having a surface treated to enhance bonding with the resin. In an embodiment, the fibres are sulphuric acid-treated glass fibres, hydrochloric acid-treated glass fibres, sulphuric and hydrochloric acid-treated glass fibres or a combination of two or more of the above. In an embodiment, the fibres are silanated glass fibres.

In a second aspect, the present invention provides a dental restoration article (e.g. a filling) made by forming and curing the dental composite of the first aspect.

In a third aspect, the present invention provides a process for producing a dental composite, the process comprising a step of mixing a polymerisable resin and fibres having a diameter of from about 3 μm to about 9 μm and a length of from about 60 μm to about 2 mm.

In an embodiment, the fibres constitute from about 0.5% to about 25% w/w of the dental composite.

In an embodiment, the diameter of the fibres is from about 3 μm to about 6 μm. In an embodiment, the mean fibre diameter is about 5 μm.

In an embodiment, the length of the fibres is from about 60 μm to about 750 μm.

In an embodiment, the aspect ratio (AR) of the fibres is from about 20 to about 200. In an embodiment, the aspect ratio (AR) of the fibres is from about 30 to about 100.

In an embodiment, the fibres comprise two or more populations of fibres, wherein the mean aspect ratio (AR) of one population of fibres is different to the mean aspect ratio (AR) of at least one other population of fibres. In an embodiment, the mean aspect ratio (AR) of one population of fibres is from about 20 to about 100, and the mean aspect ratio (AR) of the at least one other population of fibres is from about 70 to about 200.

In an embodiment, more than 80% w/w of the fibres have a length of from about 200 μm to about 500 μm.

In an embodiment, the fibres constitute from about 1% to about 10% w/w of the dental composite. In an embodiment, the fibres constitute about 5% w/w of the dental composite.

In an embodiment, the fibres are composed of glass. In an embodiment, the glass is selected from aluminosilicate glass, barium glass, fluorine glass, quartz, fused silica, borosilicate glass, aluminofluorosilicate glass, high calcium glass, high magnesium glass and mixtures thereof. In an embodiment, the glass is S-glass.

In an embodiment, the fibres are substantially randomly oriented in the dental composite.

In an embodiment, the process further comprises a fibre preparation step wherein the fibres are treated, before mixing the resin and fibres, to provide a fibre surface having improved bonding with the resin. In an embodiment, the fibres are glass fibres and the fibre preparation step comprises contacting the fibres with a strong alkali, contacting the fibres with hydrofluoric acid, contacting the fibres with phosphoric acid, contacting the fibres with sulphuric acid, contacting the fibres with hydrochloric acid, contacting the fibres with a silanating agent, plasma etching the fibres or a combination of two or more of the above. In an embodiment, the glass fibres are contacted with sulphuric acid, hydrochloric acid or a mixture thereof, and then silanated.

In an embodiment, the process further comprises a step of sonicating the mixture of fibres and resin.

In a fourth aspect, the present invention provides a dental composite prepared by the process according to the third aspect.

In a fifth aspect, the present invention provides the use of a dental composite of the first and/or fourth aspect in the restoration of a tooth.

BRIEF DESCRIPTION OF THE FIGURES

Embodiments of the present invention are described below, by way of example only, with reference to the accompanying drawings in which:

FIGS. 6(a) and 6(b) are SEM images of unprocessed fibres. FIGS. 3(c) and (d) are SEM images of hydrochloric acid processed fibres for 4 hours (c) and 24 hours (d). FIGS. 3(e) and (f) are SEM images of sulphuric acid processed fibres for 4 hours (e) and 24 hours (f).

DETAILED DESCRIPTION OF EMBODIMENTS OF THE INVENTION

In a first aspect, the present invention provides a dental composite comprising:

a polymerisable resin; and
from about 0.5% to about 25% w/w of fibres having a diameter of from about 3 μm to about 9 μm and a length of from about 60 μm to about 2 mm.

The polymerisable resin may be any polymerisable resin suitable for dental applications. Typically, dental resins are synthetic resins comprising monomers (or prepolymers). There are many commercially available dental resins that are suitable for use in the dental composite of the present invention (e.g. those that are currently used, or have been used, in dentistry restorative materials or adhesives).

Examples of polymerisable resins include resins comprising acrylates such as acrylate monomers (e.g. (mono-(meth)acrylate, di-(meth)acrylate, tri-(meth)acrylate) or dimethacrylate monomers (e.g. PEGMA, UDMA, HDDMA and TEGDMA. Other examples of polymerisable resins include ionomers such as glass ionomer cements. An ionomer is a polymer that comprises repeat units of both electrically neutral monomer units and a fraction of ionized monomer units (usually no more than 15 mole percent). Most ionomers are copolymers of neutral portions and ionized portions (usually carboxylic acid groups). Polymerisable resins are typically fluidic and easy to manipulate when in the unhardened state (uncured or wet state) and require some form of activation to initiate polymerisation to harden. Once polymerised and hardened, the resin should be insoluble in aqueous solutions (e.g. saliva) and resistant to wear (e.g. by movement of teeth).

The resins may be set or hardened (cured) by the methods known in the art. Common methods include, for example, exposure to light (e.g. at 400-470 nm), oxidation by exposure to air, oxidation by exposure to a chemical oxidant present in the resin (usually mixed into the resin immediately prior to use) or other forms of chemical reactions that initiate polymerisation of the resin.

There are many commercially available dental resins that may be used in the dental composite of the present invention. Examples of such commercially available resins include Beautifil II Universal Giomer Composite, Beautifil Flow Plus F03 Flowable Giomer and SDI Aura.

The dental composite of the present invention comprises fibres having a diameter of from about 3 μm to about 9 μm (e.g. from about 3 μm to about 8 μm, from about 3 μm to about 6 μm, from about 4 μm to about 8 μm, from about 4 μm to about 6 μm or about 5 μm) and a length of from about 60 μm to about 2 mm (e.g. from about 60 μm to about 1 mm, about 60 μm to about 750 μm, about 100 μm to about 1500 μm, about 150 μm to about 1000 μm, about 200 μm to about 1000 μm, about 200 μm to about 800 μm, about 200 μm to about 500 μm or about 200 μm to about 300 μm). The dental composite of the present invention comprises such fibres in an amount of from about 0.5% to about 25% w/w (e.g. from about 1% to about 25% w/w, about 1% to about 20% w/w, about 1% to about 15% w/w, about 1% to about 10% w/w, about 2% to about 25% w/w, about 2% to about 20% w/w, about 2% to about 15% w/w, about 2% to about 10% w/w, about 5% to about 25% w/w, about 5% to about 20% w/w, about 5% to about 15% w/w, about 10% to about 25% w/w, about 10% to about 20% w/w, about 10% to about 15% w/w, about 15% to about 25% w/w, about 15% to about 20% w/w or about 20% to about 25% w/w) based on the total weight of the dental composite. The fibres are mixed with, or dispersed in, the polymerisable resin.

In some embodiments, the inclusion of these amounts of fibres having these specific dimensions affords a dental composite that is flowable in the unhardened state (which allows the dental composite to be applied and finished more easily than EverX Posterior and the FRCs of Zakaria et al.), and has good durability and acceptable wear resistance once hardened.

Dental composites comprising fibres in higher amounts may be more difficult to work, and composites comprising fibres in lower amounts may be less durable and have less wear resistance. For example, using fibres at less than 0.5% w/w in the dental composite, a dental composite will be produced that in the hardened state is less durable and less wear resistant, whereas using more than 25% w/w of fibres in the dental composite will result in a dental composite material that is more difficult to work with and may also suffer from reduced strength in the hardened state. In some embodiments, from about 1% w/w to about 10% w/w fibres is used in the dental composite of the present invention, more preferably about 5% w/w of fibres is used in the dental composite.

In some embodiments, the fibre diameter and length have a significant effect on the properties of the dental composite. In some embodiments, the use of fibres from 60 μm to 2 mm provides for excellent mechanical properties of the cured/hardened dental composite and desirable handling properties of the uncured dental composite. Having a diameter of less than 3 μm may cause health concerns (e.g. particulate matter of less than 3 μm has previously been associated with health issues such as mesothelioma). Having a diameter greater than 9 μm negatively affects handling, manipulation and adaptation of the uncured dental composition. In an embodiment, the diameter of the fibres is from about 3 μm to about 6 μm. In an embodiment, the mean fibre diameter is about 5 μm.

Use of fibres longer than 2 mm or thicker than 9 μm also results in poorer surface qualities (e.g. voids, poor polishability, gloss and polish retention). The use of fibres having a length below about 60 μm generally provides poor mechanical properties of the cured/hardened dental composite, and the use of fibres having a length above about 2 mm generally gives dental composites having poor handling properties in the uncured state.

In some embodiments, the dental composite may also comprise some additional fibres having different dimensions to those specified above (i.e. fibres having a diameter less than 3 μm or greater than 9 μm and/or a length that is shorter than 60 μm or greater than 2 mm). In such embodiments, the fibres having a diameter of from about 3 μm to about 9 μm and a length of from about 60 μm to about 2 mm typically represent more than 50% w/w of the total fibre content (for example, more than 60% w/w, more than 70% w/w, more than 75% w/w, more than 80% w/w, more than 90% w/w, more than 95% w/w, more than 98% w/w, more than 99% w/w or more than 99.5% w/w of the total fibre content).

In embodiments where the dental composite comprises some additional fibres having different dimensions to those specified above (i.e. fibres having a diameter less than 3 μm or greater than 9 μm and/or a length that is shorter than 60 μm or greater than 2 mm), the total fibre content of the dental composite is preferably less than about 25% w/w based on the total weight of the dental composite. In other words, the total amount of fibres, including the fibres having a diameter of from about 3 μm to about 9 μm and a length of from about 60 μm to about 2 mm plus the fibres having a diameter less than 3 μm or greater than 9 μm and/or a length that is shorter than 60 μm or greater than 2 mm, is preferably less than about 25% w/w of the dental composite.

In some embodiments, more than 50% w/w (e.g. more than 80%, more than 90%, more than 95% or more than 99%) of the fibres in the dental composite have a length of from about 60 µm to about 1500 µm (e.g. about 60 µm to about 750 µm, about 100 µm to about 1500 µm, about 150 µm to about 1000 µm, about 200 µm to about 1000 µm, about 200 µm to about 800 µm, about 200 µm to about 500 µm or about 200 µm to about 300 µm).

It is believed that the aspect ratio (i.e. the ratio of the length of the fibres to the diameter of the fibres; "AR") also plays a role in providing a dental composite having desirable properties. Very low AR fibres (AR less than 10), as found in milled glass fibres, provide less desirable physical properties to the hardened FRC than fibres having a higher AR. FRCs comprising fibres having a very high AR (AR greater than 100), although strong in the hardened state, are difficult to manipulate and use in their unhardened state.

In an embodiment, the aspect ratio of the fibres is from about 20 to about 200. In an embodiment, the aspect ratio of the fibres is from about 30 to about 100.

In an embodiment, the fibres comprise two or more populations of fibres, wherein the mean aspect ratio (AR) of one population of fibres is different to the mean aspect ratio (AR) of at least one other population of fibres. By combining two or more populations of fibres, dental composites can be prepared having different properties in the uncured state and/or in the hardened state (e.g. flowability in the uncured state and strength and wear properties in the hardened state). In some embodiments, the difference in mean aspect ratio is greater than 5% (e.g. 5%-500%, 5%-200%, 5%-100%, 10%-500%, 10%-200%, 10%-100%, 50%-500%, 50%-200% or 50%-100%). In an embodiment, the mean aspect ratio (AR) of one population of fibres is from about 20 to about 100 (e.g. from about 20 to about 70, from about 50 to about 100 or from about 50 to about 70), and the mean aspect ratio (AR) of the at least one other population of fibres is from about 70 to about 200 (e.g. from about 100 to about 200, from about 70 to about 150 or from about 100 to about 150). In some embodiments, one population of fibres has the same diameter as another population of fibres, but differ in length (e.g. one population of fibres is 5 µm in diameter and about 250 µm in length (AR=50) and another population of fibres is 5 µm in diameter and about 500 µm in length (AR=100)). In some embodiments, the proportion of fibres in one population relative to the at least one other population of fibres is from about 10:1 to about 1:10 (e.g. about 5:1 to about 1:5, about 2:1 to about 1:2 or about 1:1). In some embodiments, about 50% to about 90% of the fibres have an AR of about 20 to about 100, and about 10% to about 50% of fibres have an AR of about 70 to about 200.

The fibres used in the dental composite of the present invention may be any fibres or fibrous material such as polymer fibres or glass fibres. There are various types of fibres that are commercially available and have differing diameters (and distributions of diameters). In an embodiment, the fibres are high strength fibres. High strength fibres are fibres having a tensile strength of above about 1 GPa (as measured by ASTM C1557-14) and/or a flexural strength of greater than about 150 MPa (using ISO 4049 three point flexural testing).

In some embodiments, the dental composite of the present invention comprises polymer fibres. Polymer fibres may help improve fracture toughness by utilizing controlled fibre pull out. Controlled fibre pull out is a process whereby excessive energy (generated by stresses on the tooth and/or restorative) is absorbed by the fibre being pulled out of the matrix, thereby avoiding catastrophic failure (i.e. fracture of the restorative).

In an embodiment, the fibres used in the present invention are glass fibres. Commercially available glass fibres generally have lengths greater than 2 mm. Glass fibres having a length of from about 60 µm to about 2 mm, and a desired length distribution within that range, can be prepared by a variety of techniques. The desired length of the glass fibres, and length distribution, may be obtained by, for example, cutting the long glass fibres individually. Alternatively, batch processes may be used to reduce the fibre length to the desired length. In the examples described below (Example 1 and 2), both commercially cut S2 glass fibres and glass fibres cut using an in-house made glass fibre cutting tool were used. The in-house made glass fibre cutting tool was used to individually cut the fibres to the desired length (0.25 mm to 2 mm) from lengths of glass fibre. The in-house made glass fibre cutting tool is a manually operated tool with high strength circular blades stacked together (with adjustable separation) to cut fibres to a length from 0.25 mm to 2 mm.

In an embodiment, the glass fibres may be selected from aluminosilicate glass, barium glass, fluorine glass, quartz, fused silica, borosilicate glass, aluminofluorosilicate glass, high calcium glass, high magnesium glass and mixtures thereof. In an embodiment, the glass is an S-glass (structural glass). S-glass is typically an alumino silicate glass having negligible CaO content and a high MgO content. S-glass is so named for "stiff glass", due to its high tensile strength or modulus. Examples of other types of glass, glass fibres or fibreglass that may be used include E-glass (an alumino-borosilicate glass with less than 1% w/w alkali oxides), A-glass (an alkali lime glass with little or no boron oxide), E-CR glass (an electrical/chemical resistant alumino-lime silicate glass having less than about 1% w/w alkali oxides), C-glass (an alkali-lime glass having high boron oxide content), D-glass (a borosilicate glass named for its low dielectric constant) and R-glass (alumino silicate glass having negligible MgO and CaO content used for high mechanical requirements as reinforcement).

Glass fibres are commercially available in many different diameters. Obtaining glass fibres having the desired aspect ratio typically involves selecting glass fibre having the desired diameter and cutting the length accordingly.

In some embodiments, the fibres are fibres having a surface treated to enhance bonding with the resin (e.g. surface modification). In some embodiments, the treatment to enhance bonding with the resin provides an increase in interfacial shear strength (IFSS) of the fibre in the resin in the hardened/cured state. In some embodiments, increased IFSS improves the strength and/or wear resistance of the cured dental composite. In some embodiments, the fibres are processed glass fibres, wherein the glass fibres have been processed by one or more of: contacting the glass fibres with a strong alkali (such as NaOH and KOH); contacting the glass fibres with hydrofluoric acid; contacting the glass fibres with phosphoric acid; contacting the glass fibres with sulphuric acid; contacting the glass fibres with hydrochloric acid or contacting the glass fibres with a silanating agent; especially contacting the glass fibres with sulphuric acid or hydrochloric acid. In some embodiments, the glass fibres are contacted with alkali, hydrofluoric acid, phosphoric acid, sulphuric acid, hydrochloric acid or a combination of two or more of the above. In some embodiments, the glass fibres are strong alkali-treated glass fibres, hydrofluoric acid-treated glass fibres, phosphoric acid-treated glass fibres, sulphuric acid-treated glass fibres, hydrochloric acid-treated glass fibres or a combination of two or more of the above. In some embodiments, the glass fibres are sulphuric acid-treated glass fibres, hydrochloric acid-treated glass fibres, sulphuric and hydrochloric acid-treated glass fibres or a combination of two or more of the above. In some embodiments, the glass fibres are silanated glass fibres. As referred to herein, "silanated" refers to the treatment (of the fibre) with a silanating agent (e.g. silane compound, especially a bi-functional silane compound such as 3-(trimethoxysilyl) propyl methacrylate (TMSPMA)). In some embodiments, the glass fibres are processed (e.g. treated with the alkali or acid referred to above, e.g. hydrochloric acid and/or sulphuric acid) and then silanated.

In some embodiments, the fibres are substantially randomly oriented in the dental composite. In other words, the fibres are not lined up in a continuous fashion and not aligned to any appreciable extent. Having fibres in a randomly oriented alignment leads to dental composites that do not shrink in one direction further than in other directions to an appreciable extent (isotropic strength and/or shrinkage). In other embodiments, a proportion (e.g. more than about 10%, 25%, 50%, 75%, 90%, 95% or 99%) of fibres are aligned to within about 450 degrees of each other (e.g. within about 300, 150, 100, 50 or 10 of each other) to provide anisotropic strength and/or shrinkage. Such anisotropy (e.g. alignment/parallelism) may be advantageous in certain applications, such as in the restoration and reinforcement of the middle section of the tooth (pulp chamber).

The dental composite may also comprise one or more other components, such as fillers (e.g. silica particles, quartz particles, glass particles, zirconia, ion-releasing particles, polymer particles and powdered composite particles), colourants (e.g. titanium dioxide and iron oxides), bonding agents (e.g. agents that bond or improve bonding of fibres/fillers/colourants etc. to the cured resin, such as bi-functional silane compounds), photoinitiators to initiate polymerisation of the resin (e.g. camphorquinone/amine, TPO and BAPO), catalysts to catalyse the polymerisation of the resin (e.g. photocatalysts such as titanium dioxide) and preservatives (e.g. stabilisers or inhibitors, such as BHT).

Advantageously, the dental composite of the present invention is flowable prior to polymerisation of the resin (i.e. the uncured dental composite is flowable). This gives advantageous properties such as being easy to manipulate, position and shape by a practitioner. In addition, having a flowable dental composite may lead to better and/or easier finishes, as the surface energy, optionally with the aid of gravity, allows the dental composite to bridge across gaps and fill cavities in teeth as well as advantageously allowing the formation of naturally shaped contours. In addition, such flowable dental composites may need less grinding and/or polishing in order to get a desired finished look once placed and cured in a cavity in a tooth. Previous flowable dental composites have not been recommended for use in stress bearing areas of the mouth due to strength and durability concerns.

Advantageously, the dental composites of the present invention may be produced that, when hardened, have properties similar to dentine. For example, dentine typically has flexural strength of about 260 MPa and flexural modulus of about 17 GPa.

The present invention encompasses the dental composites in their flowable unhardened (uncured) state, as well as the dental composites in their hardened (cured) state.

In a second aspect, the present invention provides a dental restoration article (e.g. a filling) made by forming and curing the dental composite of the first aspect.

In a third aspect, the present invention provides a process for producing a dental composite, the process comprising a step of mixing a polymerisable resin and fibres having a diameter of from about 3 µm to about 9 µm, and a length of from about 60 µm to about 2 mm. The mixing may be achieved by any suitable means, such as, for example, introducing fibres to the resin or adding the resin to fibres and subsequent mixing with, for example, a spatula. The method of mixing can affect the properties of the dental composite. For example, mixing by a method that introduces air bubbles may lead to dental fibres that include those air bubbles and therefore afford cured dental composites that have a lower strength. Alternatively, some methods of mixing may orient the fibres in a particular direction, which may lead to dental composites that have anisotropic strength properties. In some embodiments, FRCs comprising randomly oriented fibres are obtained by mixing techniques involving sonication (e.g. a sonicator or an ultrasonic mixer). Simple flow of the uncured dental composite tends to align the fibres. Since fibres will usually self-align in the direction of flow, methods of mixing that end with extrusion may lead to a degree of anisotropy. In some circumstances, randomly-oriented fibres in an uncured dental composite may become aligned during the material placement in a tooth. For example, fibre orientation may be affected by the delivery of the flowable material through a nozzle with a specified diameter (e.g. about 0.4 mm to about 1 mm, with smaller diameter nozzles affording greater fibre alignment).

It is believed that shorter fibres are more resistant to alignment during placement and tend to remain more randomly oriented compared to longer fibres. It is also believed that longer fibres tend to align themselves along the cavity walls and that this is more pronounced in smaller cavities.

In an embodiment, the resin is mixed with an amount of the fibres to provide a dental composite comprising the fibres in an amount of from about 0.5% to about 25% w/w of the dental composite (e.g. from about 1% to about 25% w/w, about 1% to about 20% w/w, about 1% to about 15% w/w, about 1% to about 10% w/w, about 2% to about 25% w/w, about 2% to about 20% w/w, about 2% to about 15% w/w, about 2% to about 10% w/w, about 5% to about 25% w/w, about 5% to about 20% w/w, about 5% to about 15% w/w, about 10% to about 25% w/w, about 10% to about 20% w/w, about 10% to about 15% w/w, about 15% to about 25% w/w, about 15% to about 20% w/w or about 20% to about 25% w/w), based on the total weight of the dental composite.

In an embodiment, the process further comprises a fibre preparation step wherein the fibres are treated before mixing the fibres and resin to provide a fibre surface having improved bonding with the resin. Fibres may not always adhere strongly to the resin and including a fibre preparation step acts to prepare the surface of the fibre in order to make it form stronger bonds with the resin, thereby enhancing or improving the bonding of the fibres in the resin. This can lead to fibres being more securely bonded to the resin in the hardened/cured state and improve the strength and/or wear resistance of the cured dental composite. In an embodiment, the fibres are glass fibres and the fibre preparation step is selected from contacting the glass fibres with a strong alkali, contacting the fibres with hydrofluoric acid, contacting the fibres with phosphoric acid, contacting the fibres with sulphuric acid, contacting the fibres with hydrochloric acid, contacting the fibres with a silanating agent, plasma etching the fibres or a combination of two or more of the above. The fibre preparation step may involve affecting the physical properties of the surface (e.g. roughening the surface) or may involve modifying the surface chemistry of the fibres (e.g. transforming or reacting the chemical functional groups present on the surface of the fibres) or both. Chemical transformation/modification of the surface groups can also lead to improved chemical bonding within the resin. In some embodiments, the fibres are glass fibres and the glass fibres are contacted with sulphuric acid, hydrochloric acid or a mixture thereof, and optionally, then silanated.

In an embodiment, the process further comprises a step of sonicating the mixture comprising the fibres and resin. Sonicating the mixture helps to mix the fibres and resin more uniformly. Sonicating the mixture of fibres and resin may also lead to a more random distribution of fibre orientation within the resin. Sonicating the mixture of fibres and resin also leads to a mixing that does not necessarily involve the entraining of air into the mixture. For example, sonication may mix the fibres and the resin mixture without introducing air into the mixture and may also serve to expel any entrained air bubbles from the mixture during the mixing process. Bubble removal (and improved surface wetting of fibres) may also be performed by mixing under reduced pressure.

EXAMPLES

The present invention is further described below by reference to the following non-limiting Examples.

Example 1

A "control" dental composite was used in Example 1 and Example 2. The "control" dental composite consisted of:
1,6-bis(methacryloxy-2-ethoxycarbonylamino)-2,4,4-trimethylhexane (UDMA);
triethylene glycol dimethacrylate (TEGDMA);
camphorquinone (CQ);
ethyl-4-dimethylamino benzoate (EDB); and
butylated hydroxytoluene (BHT); (total 43.4%), plus
0.7 micron strontium glass (55%); and
aerosol (1.6%).

This "control" dental composite was used as a control sample and was also used in the preparation of the fibre reinforced dental composite samples 1 to 5 described below in Examples 1 and 2.

Figure 1:
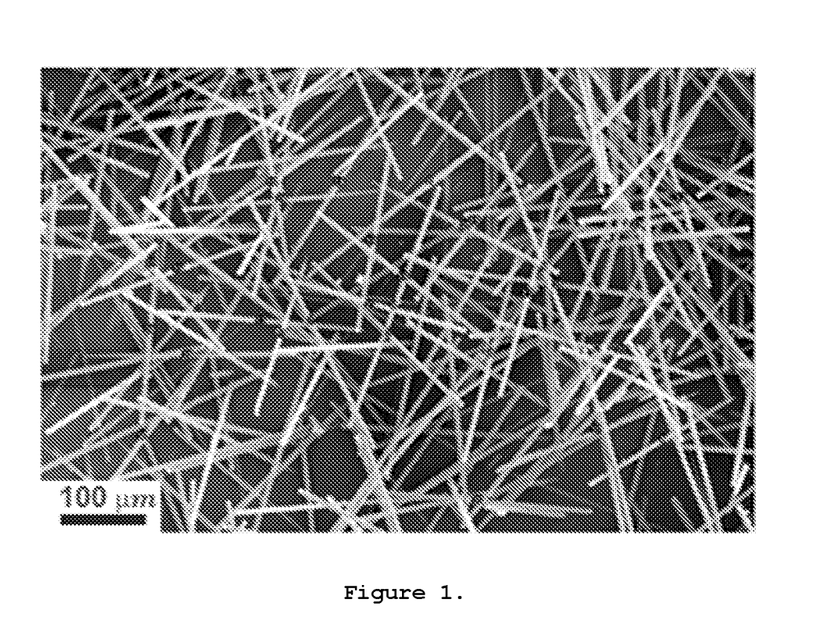
FIG. 1 is an SEM image of cut S2 glass fibres (length 0.25 mm and diameter 5 μm) used in samples 2 to 4 in Example 2.
Figure 2:
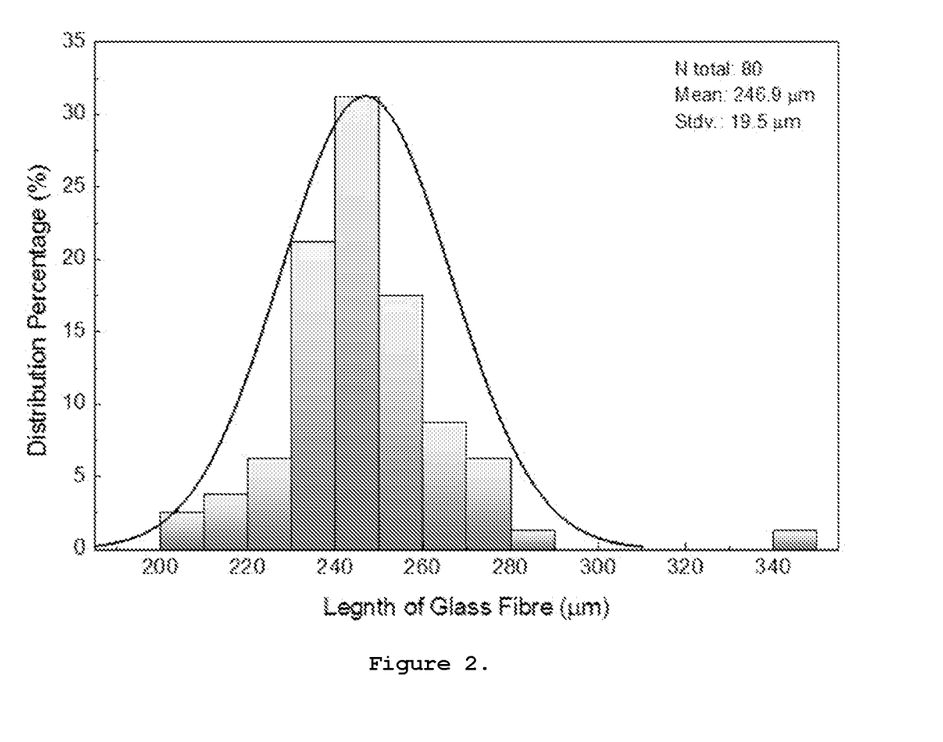
FIG. 2 is a graph showing the distribution of fibre lengths (x-axis=length of glass fibres (μm), y-axis=distribution percentage) of the cut S2 glass fibres used in samples 2 to 4, 6 and 7 in Examples 2 to 4.

A SEM image of the unprocessed S-glass fibres (representative of the S-glass fibres used in Examples 1 to 3) is presented in FIG. 1. FIG. 2 is a graph of the distribution of fibre lengths of the glass fibres used in Samples 2 to 4, 6 and 7 (described below in Examples 2 to 4).

Sample 1

Figure 3:
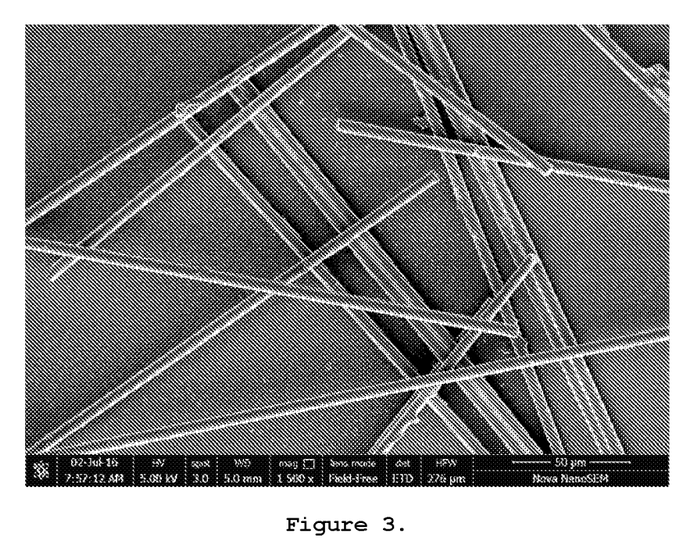
FIG. 3 is an SEM image of cut S2 glass fibres (0.5 mm long by 5 micron diameter) that have been processed as described in Example 1 and were used in the preparation of sample 1 and sample 5 as described in Example 1 and Example 2.

A fibre reinforced dental composite (sample 1) was prepared using the control dental composite and processed glass fibres (10% w/w based on the total weight of the dental composite). The processed glass fibres (etched with sulphuric acid and silanated by treatment with 3-(trimethoxysilyl) propyl methacrylate (TMSPMA) were 0.5 mm long and 5 micron in diameter. An SEM image of the processed glass fibres is presented in FIG. 3.

The control dental composite was mixed with the glass fibres manually (hand mixing with a spatula). The dental composite was then photocured using a curing lamp (wavelength 470 nm) for 15 seconds.

Figure 4:
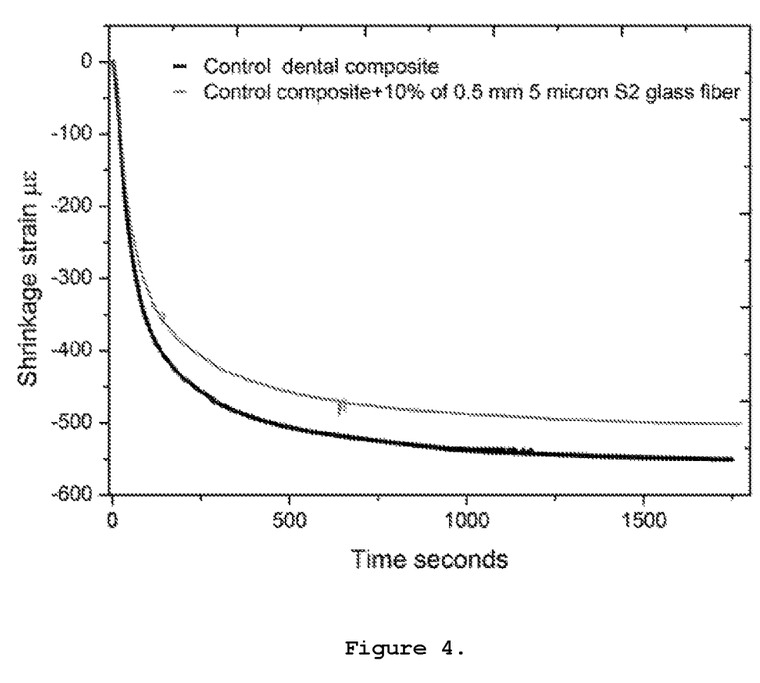
FIG. 4 is a graphical representation of the shrinkage strain (με; y-axis) over time (seconds; x-axis) and shows the curing shrinkage strain profile of sample 1 (the fibre reinforced dental composite described in Example 1 (grey line); control dental composite plus 10% w/w 0.5 mm long by 5 micron diameter S2 glass) and a "control" dental resin (black line) without fibres.

Curing shrinkage strain of the fibre reinforced dental composite (sample 1) and the "control" is shown in FIG. 4.

Example 2

Samples 2 to 5 were prepared in an analogous manner to sample 1 described above in Example 1. Samples 2 to 5 varied in the amount and dimension of glass fibres used, as set out below.

FIG. 2 is a graph of the distribution of fibre lengths of the glass fibres used in Samples 2 to 4. An SEM image of the glass fibres used in Samples 2 to 4 is presented in FIG. 1.

Sample 2
Control dental composite with 5% w/w 0.25 mm long by 5 micron diameter S2 glass.
Sample 3
Control dental composite with 10% w/w 0.25 mm long by 5 micron diameter S2 glass.
Sample 4
Control dental composite with 15% w/w 0.25 mm long by 5 micron diameter S2 glass.
Sample 5
Control dental composite with 5% w/w 0.5 mm long by 5 micron diameter S2 glass.

Figure 5:
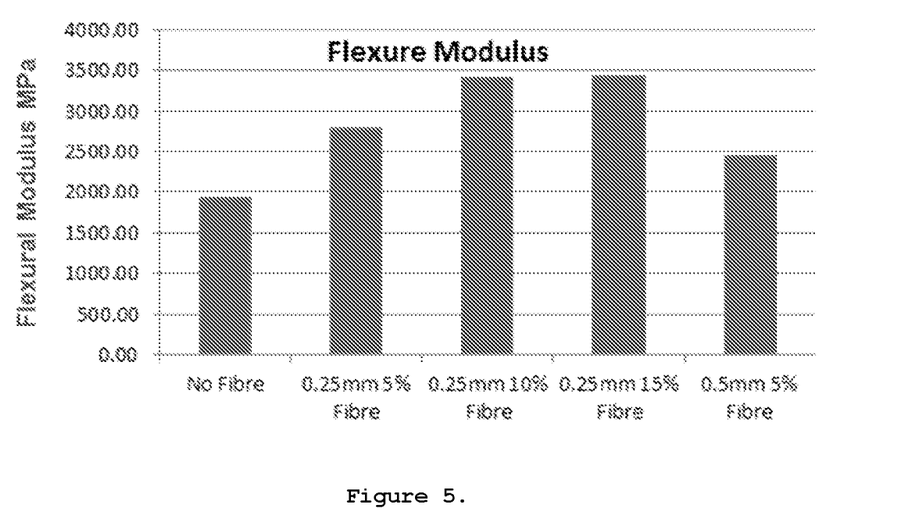
FIG. 5 is a bar graph depicting the flexural modulus (MPa) of the "control" dental resin and samples 2 to 5 as described in Example 2.

The flexural modulus of the "control" (i.e. no fibre) and samples 2 to 5 was then measured using the ISO 4049 three point flexural test method and the results are summarised in FIG. 5.

Example 3

A second control dental composite ("Control 2") was used in Example 3 and Example 4. The "Control 2" dental composite consisted of:
1,6-bis(methacryloxy-2-ethoxycarbonylamino)-2,4,4-trimethylhexane (UDMA);
triethylene glycol dimethacrylate (TEGDMA);
camphorquinone (CQ);
ethyl-4-dimethylamino benzoate (EDB); and
butylated hydroxytoluene (BHT); (total 48.4%), plus
0.7 micron strontium glass (50%); and
aerosol (1.6%).

The "Control 2" dental composite was used as a control sample and was also used in the preparation of the fibre reinforced dental composites described in Example 3, examining the effect of glass fibre surface modification on interfacial properties, and also used in the preparation of samples 6 to 9 described below in Example 4, where a fixed percentage of the filler (strontium glass) in the control composite was replaced with fibres.

Figure 6:
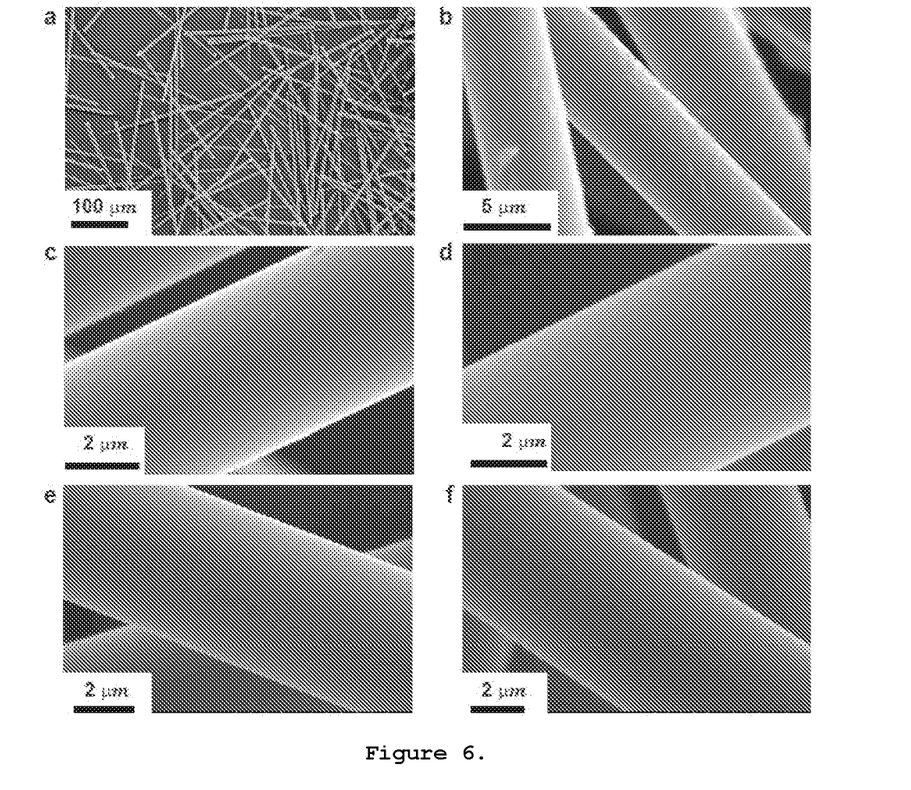
FIG. 6 is a series of SEM images of cut S2 glass fibres (0.5 mm long by 5 micron diameter) that have been processed as described in Example 3 and were used in the preparation of samples 6 to 9 as described in Example 3 and Example 4.

In Example 3, fibre reinforced dental composites were prepared using the control dental composite "Control 2" and glass fibres processed by differing methods. Glass fibres (0.5 mm long by 5 micron diameter S2 glass, AR=100 were processed using sulphuric acid or hydrochloric acid for 4 or 24 hours before being silanated by treatment with 3-(trimethoxysilyl) propyl methacrylate. SEM images of the unprocessed and processed glass fibres under these different etching conditions are presented in FIG. 6. These glass fibres were then incorporated into composites using a process analogous to the process described below in Example 4, to provide fibre reinforced dental composites.

Figure 7:
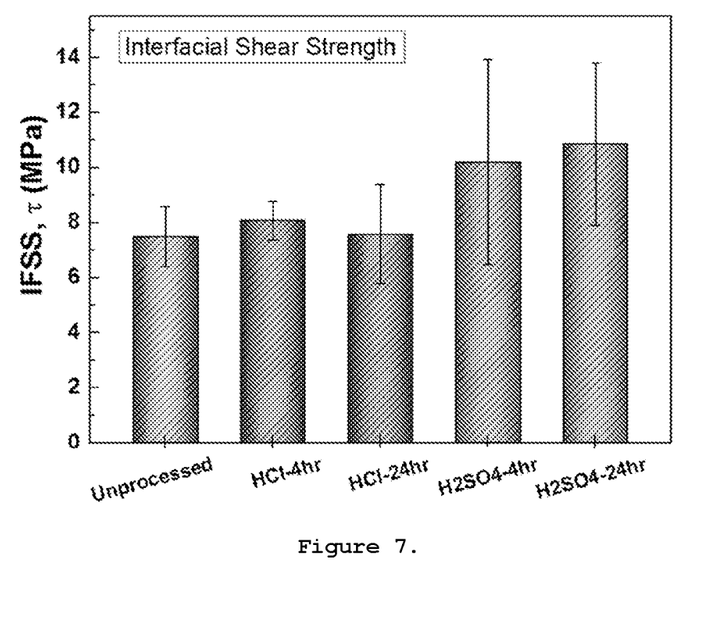
FIG. 7 is a bar graph showing the interfacial shear strength of unprocessed and processed fibres. y-axis is the interfacial shear strength (IFSS; MPa).

To evaluate the effect of glass fibre surface modification on interfacial properties, the changes in interfacial shear strength (IFSS) of fibre and resin were investigated using microdroplet pull-out tests. Microdroplet specimens were prepared by depositing a droplet of resin onto the single fibre using a micro-manipulator. After light-curing, an embedded length of the droplet was measured and ranged from 190 to 430μm. The droplet was positioned inside a micro vise (gap maintained at 20 μm) and pull-out force was measured. IFSS was calculated using the equation:

$$\tau_i = F/(\pi d_f l_e)$$

where $\tau_i$ refers to IFSS, F is the maximum load prior to the interface debonding, $d_f$ is the fibre diameter and $l_e$ is the fibre embedded length. FIG. 7 shows the interfacial shear strength of unprocessed and processed fibres (HCl, 4 h; HCl, 24 h; $H_2SO_4$, 4 h; $H_2SO_4$, 24 h), where an increase is observed for the processed fibres compared to the unprocessed fibres.

Example 4

Figure 8:
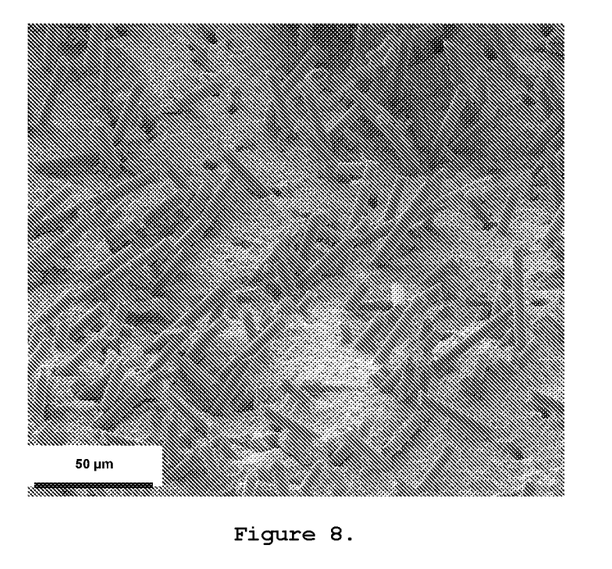
FIG. 8 is an SEM image of "Control 2" composite mixed with processed fibres (0.25 mm long by 5 micron diameter S2 glass, AR=50, 4 hour hydrochloric acid treated), which shows substantially uniform distribution of fibres within the resin with a substantially random orientation.

To prepare Samples 6 to 9, "Control 2" dental composite was mixed with processed glass fibres using an automated mixer under vacuum. The dental composite was then photocured using a curing lamp (wavelength 470 nm) for 60 seconds. FIG. 8 is an SEM image showing the distribution of processed fibres within the composite. FIG. 8 shows that the fibres are uniformly dispersed and randomly oriented in the cured composite.

Samples 6 to 9 were prepared using the method described in the above paragraph, with differing amounts and differing dimensions of glass fibres, as set out below.

Sample 6

"Control 2" dental composite with 10% w/w of strontium glass filler (based on the total weight of the composite) replaced with 10% w/w (based on the total weight of the composite) 0.25 mm long by 5 micron diameter S2 glass (AR=50) resulting in a fibre reinforced dental composite having 40% w/w strontium glass filler and 10% w/w glass fibres (based on the total weight of the composite). The fibres used in Sample 6 had been etched using hydrochloric acid for 4 hours and then silanated.

Sample 7

"Control 2" dental composite with 5% w/w of strontium glass filler (based on the total weight of the composite) replaced with 5% w/w (based on the total weight of the composite) 0.25 mm long by 5 micron diameter S2 glass (AR=50) resulting in a fibre reinforced dental composite having 45% w/w strontium glass filler and 5% w/w glass fibres (based on the total weight of the composite). The fibres used in Sample 7 had been etched using hydrochloric acid for 4 hours and then silanated Sample 8

"Control 2" dental composite with 5% w/w of strontium glass filler (based on the total weight of the composite) replaced with 5% w/w (based on the total weight of the composite) 0.35 mm long by 5 micron diameter S2 glass (AR=70) resulting in a fibre reinforced dental composite having 45% w/w strontium glass filler and 5% w/w glass fibres (based on the total weight of the composite). The fibres used in Sample 8 had been etched using hydrochloric acid for 4 hours and then silanated.

Sample 9

"Control 2" dental composite with 5% w/w of strontium glass filler (based on the total weight of the composite) replaced with 5% w/w (based on the total weight of the composite) 0.5 mm long by 5 micron diameter S2 glass (AR=100) resulting in a fibre reinforced dental composite having 45% w/w strontium glass filler and 5% w/w glass fibres (based on the total weight of the composite). The fibres used in Sample 9 had been etched using hydrochloric acid for 4 hours and then silanated.

Figure 9:
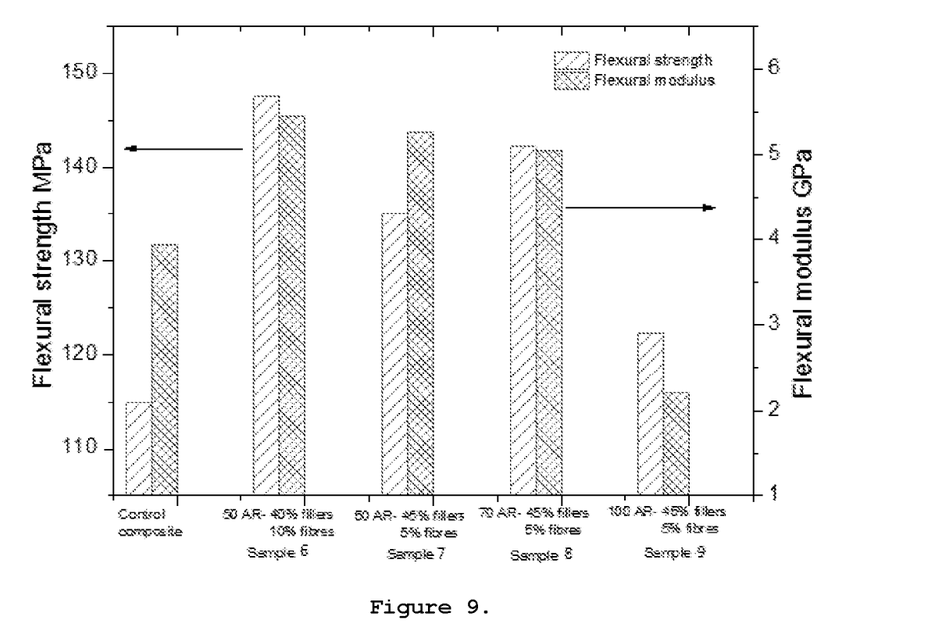
FIG. 9 is a bar graph depicting the flexural strength (MPa) and flexural modulus (GPa) of the "control" dental resin and samples 6 to 9 as described in Example 4.

The flexural strength and modulus of "Control 2" (i.e. no fibre) and samples 6 to 9 were then measured using the ISO 4049 three point flexural test method and the results are summarised in FIG. 9.

All the dental composites of the present invention (Samples 1 to 9) exhibited a higher flexural modulus than the control, and all of Samples 6 to 9 exhibited higher flexural strength than the control, indicating the greater suitability of the dental composites of the present invention for use in high stress areas.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A flowable dental composite comprising:
   a polymerisable resin; and
   from about 1% to less than 10% w/w of glass fibres having a diameter of from about 3 μm to about 6 μm and a length of from about 200 μm to about 500 μm, wherein more than 90% w/w of the fibres in the dental composite have a length of from about 200 μm to about 500 μm.

2. The dental composite according to claim 1, wherein one or more of the following applies:
   i) a mean fibre diameter is about 5 μm;
   ii) the fibres have an aspect ratio (AR) of from about 20 to about 200;
   iii) the fibres comprise two or more populations of fibres, wherein a mean aspect ratio (AR) of one population of fibres is different to the mean aspect ratio (AR) of at least one other population of fibres.

3. The dental composite according to claim 2, wherein the aspect ratio (AR) of the fibres is from about 30 to about 100.

4. The dental composite according to claim 2, wherein the mean aspect ratio (AR) of one population of fibres is from about 20 to about 100, and the mean aspect ratio (AR) of the at least one other population of fibres is from about 70 to about 200.

5. The dental composite according to claim 2, wherein the fibres constitute about 5% w/w of the dental composite.

6. The dental composite according to claim 1, wherein the glass is selected from aluminosilicate glass, barium glass, fluorine glass, quartz, fused silica, borosilicate glass, aluminofluorosilicate glass, high calcium glass, high magnesium glass, S-glass, and mixtures thereof.

7. The dental composite according to claim 1, wherein the fibres are substantially randomly oriented in the dental composite.

8. The dental composite according to claim 1, wherein the fibres are fibres having a surface treated to enhance bonding with the resin.

9. The dental composite according to claim 8, wherein the fibres are sulphuric acid-treated glass fibres, hydrochloric acid-treated glass fibres, sulphuric and hydrochloric acidtreated glass fibres, silanated glass fibres, or a combination of two or more of the above.

10. A process for producing a flowable dental composite, the process comprising a step of mixing a polymerisable resin and from about 1% to less than 10% w/w of glass fibres having a diameter of from about 3 μm to about 6 μm and a length of from about 200 μm to about 500 μm, wherein more than 90% w/w of the fibres in the dental composite have a length of from about 200 μm to about 500 μm.

11. The process according to claim 10, wherein one or more of the following applies:
   i) the mean fibre diameter is about 5 µm;
   ii) the length of the fibres is from about 200 µm to about 300 µm;
   iii) the fibres have aspect ratio (AR) of from about 20 to about 200;
   iv) the fibres comprise two or more populations of fibres, wherein the mean aspect ratio (AR) of one population of fibres is different to the mean aspect ratio (AR) of at least one other population of fibres.

12. The process according to claim 11, wherein the aspect ratio (AR) of the fibres is from about 30 to about 100.

13. The process according to claim 11, wherein the mean aspect ratio (AR) of one population of fibres is from about 20 to about 100, and the mean aspect ratio (AR) of the at least one other population of fibres is from about 70 to about 200.

14. The process according to claim 10, wherein the fibres constitute about 5% w/w of the dental composite.

15. The process according to claim 10, wherein the glass is selected from aluminosilicate glass, barium glass, fluorine glass, quartz, fused silica, borosilicate glass, aluminofluorosilicate glass, high calcium glass, high magnesium glass, S-glass, and mixtures thereof.

16. The process according to claim 10, wherein the fibres are substantially randomly oriented in the dental composite.

17. The process according to claim 10, further comprising a fibre preparation step wherein the fibres are treated, before mixing the resin and fibres, to provide a fibre surface having improved bonding with the resin.

18. The process according to claim 17, wherein the fibre preparation step comprises contacting the fibres with a strong alkali, contacting the fibres with hydrofluoric acid, contacting the fibres with phosphoric acid, contacting the fibres with sulphuric acid, contacting the fibres with hydrochloric acid, contacting the fibres with a silanating agent, plasma etching the fibres or a combination of two or more of the above.

19. The process according to claim 18, wherein the fibres are contacted with sulphuric acid, hydrochloric acid or a mixture thereof, and then silanated.

20. The process according to claim 10, further comprising a step of sonicating the mixture of fibres and resin.

21. The dental composite according to claim 1, wherein the glass is S-glass.

22. The dental composite according to claim 1, wherein the length of the fibres is from about 200 µm to about 300 µm, and wherein more than 90% w/w of the fibres in the dental composite have a length of from about 200 µm to about 300 µm.

* * * * *

UNITED STATES PATENT AND TRADEMARK OFFICE
CERTIFICATE OF CORRECTION

| | |
|---|---|
| PATENT NO. | : 11,185,476 B2 |
| APPLICATION NO. | : 16/757071 |
| DATED | : November 30, 2021 |
| INVENTOR(S) | : Prusty et al. |

It is certified that error appears in the above-identified patent and that said Letters Patent is hereby corrected as shown below:

On the Title Page (57) Abstract, Line 1: Please correct "fib-reinforced" to read -- fibre-reinforced --

(57) Abstract, Line 2: Please correct "producing and" to read -- producing, and --

In the Specification

Column 9, Line 18: Please correct "450 degrees" to read -- 45° degrees --

Column 9, Line 19: Please correct "300, 150, 100, 50, or 10" to read -- 30°, 15°, 10°, 5°, or 1° --

Signed and Sealed this
Nineteenth Day of April, 2022

Katherine Kelly Vidal
*Director of the United States Patent and Trademark Office*